US00PP20962P2

(12) United States Plant Patent
Austin

(10) Patent No.: US PP20,962 P2
(45) Date of Patent: Apr. 27, 2010

(54) ***ROSA HYBRIDA* SHRUB NAMED 'AUSBREEZE'**

(50) Latin Name: *Rosa hybrida*
Varietal Denomination: AUSbreeze

(75) Inventor: David C. H. Austin, Wolverhampton (GB)

(73) Assignee: David Austin Roses Ltd, Albrighton Wolverhampton (GB)

( * ) Notice: Subject to any disclaimer, the term of this patent is extended or adjusted under 35 U.S.C. 154(b) by 0 days.

(21) Appl. No.: 12/381,338

(22) Filed: Mar. 11, 2009

(30) Foreign Application Priority Data

Nov. 18, 2008 (GB) ..... AFP 5/2106

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para
(74) *Attorney, Agent, or Firm*—Kauth, Pomeroy, Peck & Bailey LLP

(57) ABSTRACT

A variety of rose plant of the shrub class, named 'AUSbreeze' is disclosed. The 'AUSbreeze' rose is a plant suitable for repeat flowering production having blooms that are a very pure soft pink formed in a perfect rosette formation, and having a fresh, fruity fragrance with hints of raspberry and tea. In addition, the growth of the 'AUSbreeze' variety is vigorous, tall and elegant with flowers produced along the stem.

1 Drawing Sheet

Classification: The present invention relates to a new *Rosa hybrida* shrub.

Variety denomination: The new plant has the varietal denomination 'AUSbreeze'.

ORIGIN OF INVENTION

This invention relates to a new and distinct variety of shrub rose plant named 'AUSbreeze', which was originated by crossing two unnamed, unpatented varieties of *Rosa hybrida*.

BACKGROUND OF THE INVENTION

The primary objective of this breeding was to produce a flowering variety having medium soft pink blooms in a rosette formation with strong arching growth and a fruity fragrance.

SUMMARY OF THE INVENTION

Among the features which distinguish the new variety from other presently available and commercial rose cultivars known to the inventor is the following combination of characteristics: blooms that are a very pure soft pink in a perfect rosette formation having a fresh, fruity fragrance with hints of raspberry and tea. In addition, the growth is vigorous, tall and elegant with flowers produced along the stem.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSbreeze' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent has yellow blooms with few petals, 'AUSbreeze' produces a pure soft pink bloom. The new variety is classified as a *hybrida* rose and has a vigorous, elegant arching growth.

The new variety may be distinguished from its pollen parent, by the following combination of characteristics: whereas the pollen parent bears small yellow blooms with few petals, 'AUSbreeze' bears larger blooms having many petals with a pure soft pink color.

COMPARISON WITH THE CLOSEST COMMERCIALLY AVAILABLE CULTIVAR

The closest commercially available cultivar to the new variety is the 'AUSgrab' (unpatented variety). The new rose may be distinguished from the 'AUSgrab' variety by the following combination of characteristics: the 'AUSgrab' has a shorter growth and a deeper pink color compared to 'AUSbreeze', which has a taller growth and a paler pink color. In addition, the 'AUSgrab' variety has an Old Rose fragrance, while the 'AUSbreeze' has a fruity fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of July. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2 cm long and 1.9 cm in diameter when the petals start to unfurl. Form: The bud form is pointed ovoid. Color: When sepals first divide, the bud color is Pink Group 49A. When half blown, the upper sides of the petals are Pink Group 49A with Pink Group 69D at the tips, and the lower sides of the petals are Yellow-Green Group 150C.

*Calyx.*—Shape: Curls right back over receptacle. Length: 2 cm. Diameter: 1.8 cm.

*Sepals.*—Arrangement: Regular. Color: Upper Surface: Yellow-Green Group 144B with some Red-Purple Group 58A. Lower Surface: Greyed-Green Group 194B with some Red-Purple Group 58A. Length: 21 mm. Width: 7 mm. Shape: Pointed. Margin: Hairy. Surface texture: Upper Surface: Smooth. Lower Surface: Hairy. Number: There are three heavily appendaged sepals. There are two unappendaged sepals with hairy edges.

*Receptacles.*—Color: Green Group 141C. Shape: Funnel. Size: Small, about 1 cm tall×0.8 cm wide. Surface: Smooth.

*Peduncle.*—Length: Medium, averaging about 5.5 cm. Surface: Glandular. Color: Greyed-Red Group 181A. Strength: Strong.

*Blooms.*—Size: Medium, average open diameter is about 8 cm. Borne: Several together in clusters of 4–6 blooms having a flat shape. Stems: Strength: Strong, average length is about 80 cm. Diameter: 3 mm. Form: When first open, bloom is cupped. Permanence of bloom: retains its form to the end.

*Petalage.*—Number of petals under normal conditions: about 95. Color: The upper sides of the petals are Pink Group 49D. The reverse sides of the petals are Pink Group 49D. The base of the petals has a spot of Yellow-Green Group 150D. Discoloration: The general tonality at the end of the first to third days is Pink Group 49D. Fragrance: Moderate. Character of fragrance: Fruity.

*Petals.*—Texture: Velvety. Size: Width: 3 cm. Length: 3.9 cm. Surface: Smooth. Shape: Round (outer petals); Obovate (inner petals). Margin: Reflexing is weak and undulation is very weak. Apex Shape: Notched (outer petals); Rounded (all others). Base Shape: Pointed. Form: Incurved. Arrangement: Imbricated. Petaloids: Number: 2. Color: Pink Group 49D; Length: 10 mm. Width: 3 mm. Shape: Irregular. Margin: Irregular. Persistence: Petals drop off cleanly before drying. Lastingness: On the plant: fair, about 5 days. As a cut flower: not tested.

*Reproductive parts.*—Stamens: Number: 5. Length: 5 mm. Anthers: Length: 1.5 mm. Color: Red-Purple Group 60B. Arrangement: Tucked in calyx or partly so. Filaments: Color: Yellow Group 160C. Length: 3 mm. Pollen: Color: Greyed-Red Group 175A. Pistils: Number: 24. Length: 5 mm. Styles: Color: Yellow-Green Group 154C. Length: 5 mm. Stigmas: Color: Yellow Group 13B. Length: 10 mm. Hips: None Observed.

Plant characteristics:

*Plant form.*—Shrub.

*Plant growth.*—Vigorous and arching.

*Age to maturity.*—Two years.

*Mature plant.*—Height: 1.5 m. Width: 1.5 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves: 5–7 (including terminal leaflet). Size: Medium, about 13.5 cm long×9 cm wide. Quantity: Normal. Number of leaves per flowering stem: 9. Color: New foliage: Upper side: Yellow Group 143A, overlaid with Greyed-Red Group 181A. Lower side: Yellow Group 143A overlaid with Green Group 181A. Old foliage: Upper side: Green Group 136A. Lower side: Green Group 137B.

*Leaflets.*—Size: About 5.2 cm long×3.6 cm wide. Shape: Oval. Base Shape: Rounded. Apex Shape: Acuminate. Texture: Leathery. Edge: Serrated. Serrations: Single. Petiole: Color: Green Group 137A. Length: 4.5 cm. Width: 2 mm. Surface Texture: Smooth with an occasional prickle. Petiole Rachis: Color: Green Group 137A. Underside: With occasional prickles. Stipules: Length: 3 cm, hairy. Color: Green Group 137A. Auricle: Shape: Pointed. Length: 8 mm. Width: 1.5 mm. Color: Green Group 137A. Vein Color: As leaf color Green Group 137A. Venation Pattern: Net-veined.

*Wood.*—New Wood: Color: Greyed-Red Group 181A. Bark: Smooth. Old Wood: Color: Green Group 137C. Bark: Smooth.

*Branching habit.*—Number: 8 per main stem. Lateral Branch Dimensions: Length: 35 cm. Diameter: 4 mm.

*Stems.*—Mature Stem: Length: 80 cm. Diameter: 5 mm. Internode Distance: 6–8 cm. The above measurements are all variable, depending on growing conditions in a season. Stem Pubescence Present: No.

*Prickles.*—Quantity: On main canes from base: Ordinary. Number per stem length: 10 per 10 cm. On laterals from main canes: Ordinary. Number per stem length: 8 per 10 cm. Form: Deep concave. Length: 8 mm. Color when young: Greyed-Red Group 181A. Color when mature: Greyed-Red Group 182C with Green Group 138C.

*Small prickles.*—Quantity: Main stalk: None. Laterals: None.

*Disease resistance.*—Mildew: Resistant. Blackspot: Resistant. Rust: Resistant.

*Pest resistance.*—Not tested.

*Winter hardiness.*—Not tested.

*Growing conditions.*—Normal.

What is claimed is:

1. A new and distinct variety of rose plant of the shrub class suitable for repeat flower production, substantially as herein shown and described.

* * * * *

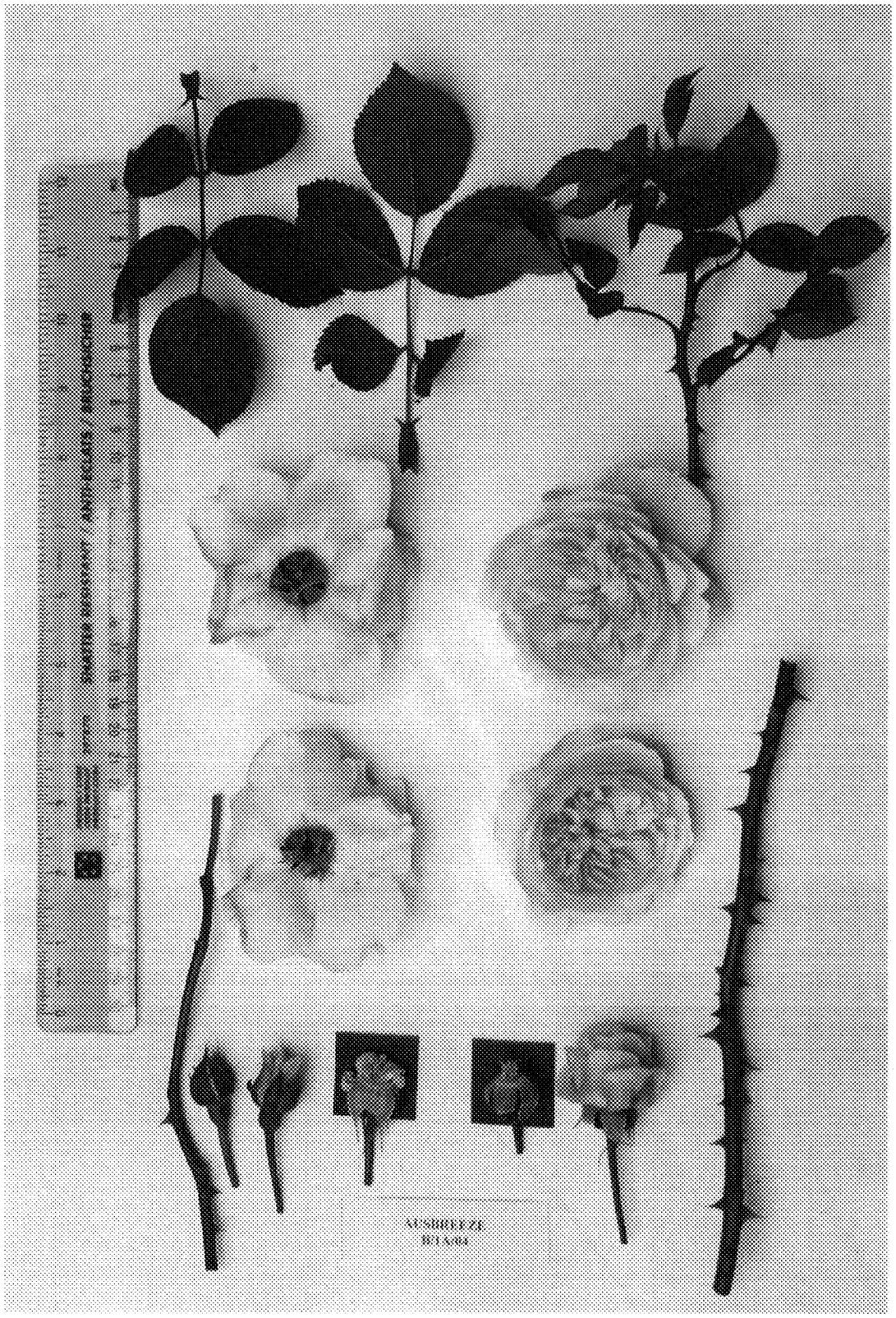
AUSBREEZE
BEAGRI